United States Patent [19]
Hutchinson et al.

[11] Patent Number: 6,031,139
[45] Date of Patent: Feb. 29, 2000

[54] PREPARATION OF α-FLUOROKETONES

[75] Inventors: John Hutchinson, Wynd; Richard Dickinson Chambers, Whitesmocks, both of United Kingdom

[73] Assignee: F2 Chemicals Limited, United Kingdom

[21] Appl. No.: 09/011,415

[22] PCT Filed: Jun. 6, 1997

[86] PCT No.: PCT/GB97/01547

§ 371 Date: Feb. 5, 1998

§ 102(e) Date: Feb. 5, 1998

[87] PCT Pub. No.: WO97/46508

PCT Pub. Date: Dec. 11, 1997

[30] Foreign Application Priority Data

Jun. 7, 1996 [GB] United Kingdom .................. 9611869

[51] Int. Cl.$^7$ ..................................................... C07C 45/54
[52] U.S. Cl. ........................... 568/356; 568/319; 568/321; 568/361; 568/398; 568/403
[58] Field of Search ..................................... 568/356, 398, 568/319, 322, 361, 403

[56] References Cited

U.S. PATENT DOCUMENTS 5,243,080  9/1993  Van Der Puy et al. ................. 568/356

OTHER PUBLICATIONS

"Preparation of α–Fluoroaldehydes and α–Fluoroketones Using Dilute Fluorine," Purrington et al., *Tetrahedron Letters*, vol. 27, No. 24, pp. 2715–2716, 1986.

*Primary Examiner*—James H. Reamer
*Attorney, Agent, or Firm*—Kolisch, Hartwell, Dickinson, McCormack & Heuser

[57] ABSTRACT

The use of polar organic solvent as the solvent in the direct fluorination, to make an α-fluoroketone, of an enol ester or enol trialkylsilyl ether of a compound containing a tautomerisable ketone group, the solvent being relatively inert to fluorine and one in which the enol ester or enol trialkylsilyl ether is relatively stable to hydrolysis. Preferably the solvent is anhydrous, e.g. anhydrous acetonitrile. Alternatively commercial formic acid containing 3% water may be used with a said enol ester.

38 Claims, No Drawings

PREPARATION OF α-FLUOROKETONES

This invention relates to the preparation of α-fluoroketones.

α-Fluoroketones are valuable compounds, both as intermediates in the preparation of biologically active molecules and as biologically active molecules in their own right. There is no satisfactory direct method of replacing the α-hydrogen of a ketone by fluorine, but by first making an enol ester or a trialkylsilyl ether of the parent ketone, and then treating either of these with an electrophilic fluorinating agent, good yields of α-fluoroketone can be obtained.

Examples of published attempts to prepare α-fluoroketones include the following:

1. The treatments of enol esters with reagents such as:
   a) $CF_3COF/CF_3CF_2OF$ (S Rozen and Y Menachem, *J Fluorine Chem.* 1980, 16, 19)
   b) N-fluoropyridinium pyridine heptafluorodiborate (A J Poss, M Van Der Puy, D Nalewajek, G A Shia, W J Wagner and R L Frenett; *J Org Chem,* 1991, 56, 5962)
   c) xenon difluoride, caesium fluoroxysulphate (S Stavber, B Sket, B Zajc and M Zupan; *Tetrahedron,* 1989, 45, 6003)
   d) 1-(chloromethyl)4-fluoro-1,4-diazabicyclo[2,2,2]octane bis (tetrafluoroborate) (G S Lal; *J Org Chem,* 1993, 58, 2791)

2. The treatments of silyl ethers with reagents such as:
   a) xenon difluoride (G L Cantrell and R Filler; *J Fluorine Chem,* 1985, 27, 35 and T Tsushima, K Kawada and T Tsuji; *Tetrahedron Letters,* 1982, 23, 1165)
   b) $CF_3OF$ (W J Middleton and E M Bingham, *J Am Chem Soc,* 1980, 102, 4846)
   c) N-fluorobenzenesulphonimide (E Differding and H Ofner, *Synlett,* 1991, 187)
   d) 1-(chloromethyl)4-fluoro-1,4-diazabicyclo[2,2,2]octane bis(tetrafluoroborate) (G S Lal; *J Org Chem,* 1993, 58, 2791)
   e) N-fluoropyridinium salts (T Umemoto, S Fukami, G Tomizawa, K Harasawa, K Kawada and K Tomita; *J Am Chem Soc,* 1990, 112, 8563).

These electrophilic fluorinating agents are often difficult to prepare and sometimes difficult to handle, or they are expensive to obtain. The use of elemental fluorine for such fluorinations would seem to afford certain advantages. When enol acetates have been treated with fluorine in the past. "no matter how mild the conditions used the reaction resulted in a very complicated mixture and no α-fluoroketones could be detected". (S Rozen and Y Menachem: *J Fluorine Chem* 1980, 16, 19).

The use of elemental fluorine for the fluorination of trialkylsilyl ethers has been attempted by G L Cantrell and R Filler (*J Fluorine Chem,* 1985, 27, 35) and by S Purrington, N V Lazaridis and C L Bumgardner (*Tetrahedron Letters,* 1986, 27, 2715). Cantrell et al found that when a dichloromethane solution of the trimethylsilylenol ether of cyclohexanone was treated with elemental fluorine, only cyclohexanone was obtained. Purrington et al was successful in obtaining α-fluoroketones but their reactions were carried out at −78° C. and the solvent was chlorotrifluoromethane. Accordingly the reactions were carried out at a temperature which is expensive to maintain and in a solvent which has been banned under the terms of the Montreal Protocol on the use of chlorofluorocarbons.

Surprisingly we have now found that enol esters and trimethylsilyl ethers of ketones can be treated with elemental fluorine at ambient temperatures in convenient, available solvents to give α-fluoroketones in good yields. In one aspect this invention is the use of a polar organic solvent in the direct fluorination, to make an α-fluoroketone, of an enol ester or enol trialkylsilyl ether of a compound containing a tautomerisable ketone group, the solvent being relatively inert to fluorine and one in which the selected ester or ether is relatively stable to hydrolysis. Enol esters are preferred over trialkylsilyl ethers.

According to the present invention there is more particularly provided a process for the preparation of an α-fluoroketone of formula R—CHFC=O.R' which includes the steps of converting a ketone of formula R—$CH_2$C=O.R' into a ketone derivative which is an enol ester of formula R—CH=C(OCO.R")R' or is a trialkylsilyl ether of formula R—CH=C(OSiR"$_3$).R', followed by the reaction of that ketone derivative, dissolved in a polar organic solvent which is relatively inert towards fluorine and in which the ketone derivative is relatively stable to hydrolysis, with elemental fluorine. The essence of the substrate, however, is that it is a compound containing an enol ester or enol trialkylsilylether of a tautomerisable ketone function and, except for the double bond of the enol group, relatively resistant to fluorination.

In the above formulae, the groups R and R' are independently selected from alkyl, substituted alkyl, cycloalkyl, substituted cycloalkyl, aryl and substituted aryl, said groups R and R' being optionally joined to one another to form a cyclic structure such as a steroid, an example being the enol acetate derived from a cholestanone, especially 5α-cholestan-3-one.

Suitable substituents include another of the R/R' groups; for example, alkyl may be substitued by cycloalkyl or aryl or aryl substituted by alkyl. Also suitable are halogen (e.g. chlorine or fluorine), alkoxy and aryloxy, as well as other groups which are relatively inert to fluorine. Any of the aforegoing substituents may be substituted in turn by one or more other suitable substituents, to form groups such as, for example, haloalkoxy or alkoxyaryl. The group R" is alkyl or cycloalkyl. Preferably R and R' contain up to 10 carbon atoms. Preferably, R" has from 1 to 4 carbon atoms.

The conversion of the ketone into the enol ester or the trialkylsilyl ether may be carried out by any of the methods known to those familiar with the art. For example, the enol acetate (R" is $CH_3$) may be made by treating the parent ketone with acetic anhydride and acetic acid, or with isopropenyl acetate in the presence of a catalyst such as p-toluene sulphonic acid. The conversion of the ketone into the trialkylsilyl ether, may be carried out by methods such as those described by H O House, L J Czuba, M Gall and H D Olmstead; *J Org Chem* 1969, 34, 2324, or D T W Chu and S N Huckin; *Canad J Chem,* 1980,58, 138 and references cited therein.

The fluorination step may be carried out by contacting fluorine gas, normally diluted with an inert gas such as nitrogen or argon, with a solution of the enol ester or trialkysilyl ether in a polar organic solvent which is relatively inert towards fluorine.

Preferably the solvent should have high polarity, for example a polarity similar to acetonitrile or formic acid. In one class of processes the polar solvent is not dry but, nonetheless, the ketone derivative (ether or ester) is relatively stable to hydrolysis in it; for example, commercially available formic acid contains 2–3% water, which water causes significant hydrolysis of trialkylsilyl ethers of ketones but not of their enol esters.

The solvent is not only one in which the substrate (i.e. ketone derivative) remains relatively stable to hydrolysis but is also relatively inert towards fluorine. That is to say, a majority of the fluorine in the reaction mixture reacts with the substrate rather than with the solvent and a majority of the substrate reacts with fluorine rather than with water. Of course, if the solvent is substantially anhydrous then the question of hydrolysis does not arise.

In one class of embodiments, the solvent is an alkane nitrile, especially acetonitrile or, less preferably, propionitrile. In another class of embodiments, the solvent is an alkanoic acid, especially formic acid. The invention does not exclude other solvent compounds or mixtures although the skilled reader will be aware that a solvent is a substance which does not react significantly with the reagents.

The reaction may be carried out by passing the fluorine gas (usually diluted) through a stirred solution of the enol ester or trialkysilyl ether or a stream of a solution of these substrates may be contacted with the fluorine gas in a concurrent or countercurrent manner.

The fluorination process may be carried out at a temperature of from −45° C. to +80° C. Preferably, it is carried out at a temperature of from −20° C. to +30° C. The concentration of fluorine is preferably from 1% to 50% by volume, more preferably from 2% to 25% by volume and most preferably from 5% to 15% by volume.

The ratio of fluorine to enol ester (or trialkysilyl ether) may be varied within wide limits although it is preferred that the molar ratio of fluorine to substrate is from 0.5:1 to 6:1 and more preferably from 0.8:1 to 3:1. The use of a higher ratio of fluorine to substrate ensures that all of the substrate is converted into the α-fluoroketone.

After the fluorination reaction has been performed, the end product may be hydrolysed to convert the substituted enol function to a ketone. More particularly, when the fluorination reaction is complete, the products may be isolated by purging the system with inert gas. This may be followed by contacting the reaction mixture with water or a dilute mineral acid. The α-fluoroketone may then be extracted from the aqueous mixture with a suitable organic solvent such as dichloromethane. The product may then be isolated by removing the solvent from the extracts by distillation followed by an appropriate purification of the residue such as by distillation, chromatography, recrystallisation or a combination of these procedures.

Thus, the α-fluoroketone is usually recovered from the reaction mixture as part of the fluorination process. It may be subjected to one or more further process to make a subsequent end product, or alternatively, formulated into a preparation.

The invention includes a process for the preparation of an α-fluoroketone, comprising directly fluorinating, to make an α-fluoroketone, an enol ester or enol trialkylsilyl ether of a compound containing a tautomerisable ketone group, the ester or ether being in a polar organic solvent which is relatively inert to fluorine and one in which the enol ester or enol trialkylsilyl ether is relatively stable to hydrolysis.

Embodiments of the present invention will now be described, by way of example only.

EXAMPLE 1

Through a stirred solution of 1-cyclohexenyl acetate (3.5 gm, 25 mmol) in dry acetonitrile (50 ml) was bubbled fluorine (50 mmol diluted to 10% v/v with nitrogen) over 110 mins. The reaction temperature was maintained at about 0° C. by cooling the reaction vessel externally. When the reaction was complete, the fluorine was switched off and the vessel was purged with nitrogen. The reaction mixture was then poured into water and thoroughly shaken before being extracted with dichloromethane. Most of the solvent was removed from the dried extracts under reduced pressure using a rotary evaporator. The residue was then distilled under reduced pressure using a short path distillation apparatus to give a main fraction (2.3 gm) which contained one major component (77% of total area of chromatogram) and several minor ones. A sample of the main component was isolated by preparative scale gas chromatography and identified as 2-fluorocyclohexanone ($^{19}$F NMR δ−188.7 ppm, d, $J_{HF}$48.7 Hz. $^1$H NMR δ 4.96 ppm, dq, $J_{HF}$49 Hz, $J_{HH}$5.9 Hz, Multiplets at 2.6, 2.4, 2.1 and 1.7 ppm, M+ 116). Yield of 2-fluorocyclohexanone=61%.

EXAMPLE 2

Through a stirred solution of 1-(trimethylsiloxyl)-cyclohexene (3.4 gm, 20 mmol) in dry acetonitrile (50 ml) was bubbled fluorine (60 mmol diluted to 10% v/v with nitrogen) over 180 mins. The reaction temperature was maintained at about 0° C. by cooling the reaction vessel externally. When the reaction was complete, the fluorine was switched off and the vessel was purged with nitrogen. The reaction mixture was then poured into water and thoroughly shaken before being extracted with dichloromethane. Most of the solvent was removed from the dried extracts under reduced pressure using a rotary evaporator. The residue was then distilled under reduced pressure using a short path distillation apparatus to give a mixture of solvent (46%), cyclohexanone (2%), 2-fluorocyclohexanone (42%) and some minor components. Cyclohexanone and 2-fluorocyclohexanone were identified by gc/ms and in the case of the fluoro-compound, also by its $19_F$ NMR spectrum. Yield of 2-fluorocyclohexanone=45%.

EXAMPLE 3

In a similar manner to that outlined in Example 1, 20 mmol of 1-cyclooctenyl acetate dissolved in acetonitrile was treated with 50 mmol fluorine over 110 min. On work up, the main product was identified as 2-fluorocyclooctanone (HRMS; Found, 144.0950; $C_8H_{13}$FO requires 144.0950; $δ_F$ 191.6 (m); $δ_H$ 1.36–2.7 (m, 12 H), 4.9 (dm, $J_{,H,F}$49.5, 1 H); $δ_C$ 20.5 (d, $^3J_{C,F}$3.6, C4), 24.6 (d, $^3J_{C,F}$3.7, C8), 24.7 (s), 27.2 (s), 32.7 (d, $^2J_{C,F}$21, C3), 39.6 (s), 91.5 (d, $^1J_{C,F}$184.7 C2), 213.9 (d, $^2J_{C,F}$20.9, C1); m/z 144 (M+, 3%) 55 (100)). Yield of 2-fluorocyclooctanone=66%.

EXAMPLE 4

In a similar manner to that outlined in Example 3, 20 mmol of 4-nonenyl-5-acetate was treated with 50 mmol fluorine over 110 min. On work up, the main product was identified as 4-fluoro-5-nonanone (HRMS; Found,160.1263; $C_9H_{17}$FO requires 160.1263; δF−193 (m); δH 0.94 (m, 6 H), 1.2–1.9 (m, 8 H), 4.7 (ddd, $J_{H,F}$49.5, $J_{H,F}$6, $J_{H,F}$6, 1 H); δc 13.6 (s, CH$_3$), 13.8 (s,CH$_3$), 17.9 (s), 22.3 (s), 24.7 (s), 34 (d, $^2J_{C,F}$20.5, CHF.CH$_2$), 37.7 (s, CH$_2$CO), 95.9 (d, $^1J_{C,F}$182.5, CHF), 210.5 (d, $^2J_{C,F}$24.1, CO), m/z 160 (M+, 6%), 57 (100). Yield of 4-fluoro-5-nonanone=61%.

EXAMPLE 5

In a similar manner to that outlined in Example 3, 20 mmol of 4-tert-butyl-1-cyclohexenyl acetate was treated with 50 mmol fluorine over 110 min. On work up, the main product was identified as a mixture of cis and trans 2-fluoro-tert-butyl cyclohexanone (δF−186 (tm) (trans), 188.7 (dm) (cis). GC/MS showed two compounds, having significantly different retention times. m/z 172. The literature (N. L.

Allinger and H. M. Blatter; J. Org. Chem., 1962. 27. 1523, S. Rozen and Menahem, J. Fluorine Chem., 1980, 16, 19; B. Zajc and M. Zupan, J. Org. Chem., 1982, 47. 573.) suggests that the compound with the shorter retention time is trans 2-fluoro-4-tert-butyl cyclohexanone and the other is the cis isomer). Yield cis and trans 2-fluoro-4-tert-butyl cyclohexanone=45%.

EXAMPLE 6

In a similar manner to that outlined in Example 2, 20 mmol of 1-(trimethylsiloxy)-cyclooctene was treated with 50 mmol fluorine over 110 min. On work up, the main product was identified as 2-fluorocyclooctanone. Yield=23%.

EXAMPLE 7

In a similar manner to that outlined in Example 6, 20 mmol of 5-(trimethylsiloxy) 4-nonene was treated with 50 mmol fluorine over 110 min. On work up, the main product was identified as 4-fluoro-5-nonanone. Yield=35%.

EXAMPLE 8

In a similar manner to that outlined in Example 1, 20 mmol of 2-cyclohexenyl acetate dissolved in 50 ml formic acid was treated with 64 mmol fluorine over 240 min. On work up, the main product was identified as 2-fluorocyclohexanone. Yield=71%.

EXAMPLE 9

In a similar manner to that outlined in Example 8, 20 mmol of 1-cyclooctenyl acetate dissolved in 50 ml formic acid was treated with 64 mmol fluorine over 240 min. On work up, the main product was identified as 2-fluorocyclooctanone. Yield=61%.

EXAMPLE 10

In a similar manner to that outlined in Example 8, 20 mmol of 4-tert-butyl-1-cyclohexenyl acetate dissolved in 50 ml formic acid was treated with 64 mmol fluorine over 240 min. On work up, the main product was identified as a mixture of cis and trans 2-fluoro-4-tert-butyl cyclohexanone. Yield=46%.

EXAMPLE 11

In a similar manner to that outlined in Example 8, 20 mmol of 4-nonenyl-5-acetate dissolved in 50 ml formic acid was treated with 64 mmol fluorine over 240 min. On work up, the main product was identified as 4-fluoro-5-nonanone. Yield=71%.

We claim:

1. A process for the preparation of an α-fluoroketone which comprises fluorinating with elemental fluroine an enol compound selected from the group consisting of enol esters and enol trialkylsilyl ethers of, in either case, compounds containing a tautomerisable ketone group, the enol compound being dissolved in a polar organic solvent which is relatively inert to fluorine and in which the enol compound is relatively stable to hydrolysis.

2. A process according to claim 1 wherein the elemental fluorine is fluorine gas diluted with an inert gas.

3. A process according to claim 2 wherein the inert gas is nitrogen or argon.

4. A process according to claim 2 wherein the fluorine gas is present in the inert gas/fluorine mixture in an amount of from 1% to 50% by volume.

5. A process according to claim 3 wherein the fluorine gas is present in the mixture in an amount of from 5% to 15% by volume.

6. A process according to claim 1 wherein the solvent has a high polarity.

7. A process according to claim 1 wherein the solvent has a polarity of which formic acid or acetonitrile is representative.

8. A process according to claim 1 wherein the solvent is an alkane nitrile containing up to four carbon atoms or an alkanoic acid containing up to four carbon atoms.

9. A process according to claim 1 wherein the solvent is acetonitrile.

10. A process according to claim 1 wherein the solvent is formic acid.

11. A process according to claim 1 wherein the solvent is substantially anhydrous.

12. A process according to claim 11 wherein the solvent is acetonitrile or formic acid.

13. A process according to claim 1 wherein the solvent contains a small amount of water, and the enol compound is a said enol ester.

14. A process according to claim 13 wherein the solvent is formic acid.

15. A process according to claim 1 which is carried out at a temperature of from −45° C. to +80° C.

16. A process according to claim 8 which is carried out at a temperature of from −20° C. to +30° C.

17. A process according to claim 2 wherein the molar ratio of fluorine to the enol compound is from 0.5:1 to 6:1 and the solvent is acetonitrile or formic acid.

18. A process according to claim 1 wherein, when the fluorination reaction is complete, the reaction mixture is contacted with water or a dilute mineral acid to convert the enol function to a ketone.

19. A process according to claim 1 wherein the enol compound is of the formula R—CHFC=O. R' wherein R and R' are independently selected from alkyl, substituted alkyl, cycloalkyl, substituted cycloalkyl, aryl and substituted aryl, said substituents being another R/R' group, halogen, alkoxy or aryloxy, or wherein groups R and R' together form a cyclic structure, and R" is alkyl or cycloalkyl, said enol ester being of the formula R—CH=C(OCO.R")R' and said trialkylsilyl ether being of the formula R—CH=C(OSiR"$_3$).R'.

20. A process according to claim 19 wherein the solvent has a polarity of which formic acid or acetonitrile is representative, the elemental fluorine is fluorine gas diluted with an inert gas, and the process is carried out at a temperature of from −45° C. to +80° C.

21. A process for the preparation of an α-fluoroketone which comprises fluorinating with elemental fluorine an enol compound selected from the group consisting of enol esters and enol trialkylsilyl ethers of, in either case, compounds containing a tautomerisable ketone group, the enol compound being dissolved in a polar organic solvent which is an alkane nitrile containing up to four carbon atoms or an alkanoic acid containing up to four carbon atoms, provided that the solvent is anhydrous or, alternatively, that the solvent contains a small amount of water and the enol compound is a said enol ester atoms, provided that the solvent is anhydrous or, alternatively, that the solvent contains a small amount of water and the enol compound is a said enol ester.

22. A process according to claim 21 wherein the elemental fluorine is fluorine gas diluted with an inert gas, the solvent is acetonitrile or formic acid and said small amount of water is not more than 3%.

23. A process according to claim 21 wherein the enol compound is of the formula R—CHFC=O.R' wherein R and R' are independently selected from alkyl, substituted alkyl, cycloalkyl, substituted cycloalkyl, aryl and substituted aryl, said substituents being another said R/R' group, halogen, alkoxy or aryloxy, or wherein groups R and R' together form a cyclic structure, and R" is alkyl or cycloalkyl, said enol ester being of the formula R—CH=C(OCO.R")R' and said trialkylsilyl ether being of the formula R—CH=C(OSiR"$_3$).R'.

24. A process according to claim 23 wherein the solvent is acetonitrile, R and R' contain up to 10 carbon atoms, and R" has from 1 to 4 carbon atoms.

25. A process for the preparation of an α-fluoroketone of formula R—CHFC=O.R' which includes the steps of converting a ketone of formula R—CH$_2$C=O.R' into a ketone derivative which is an enol ester of formula R—CH=C(OCO.R")R' or is a trialkylsilyl ether of formula R—CH=C(OSiR"$_3$).R', followed by the reaction of that ketone derivative, dissolved in a polar organic solvent which is relatively inert towards fluorine and in which the ketone derivative is relatively stable to hydrolysis, with elemental fluorine, the groups R and R' being independently selected from alkyl, substituted alkyl, cycloalkyl, substituted cycloalkyl, aryl and substituted aryl, said groups R and R' being optionally joined to one another to form a cyclic structure, and the group R" being alkyl or cycloalkyl.

26. A process according to claim 25 wherein R and R' contain up to 10 carbon atoms and R" has from 1 to 4 carbon atoms.

27. A process according to claim 25 wherein R and R' are independently selected from alkyl, cycloalkyl and aryl, said groups R and R' being optionally joined to one another to form a cyclic structure.

28. A process according to claim 25 wherein the elemental fluorine is fluorine gas diluted with an inert gas.

29. A process according to claim 25 wherein the solvent has a high polarity.

30. A process according to claim 25 wherein the solvent is acetonitrile.

31. A process according to claim 25 wherein the solvent is formic acid.

32. A process according to claim 25 wherein the solvent is substantially anhydrous.

33. A process according to claim 32 wherein the solvent is formic acid.

34. A process according to claim 25 wherein the solvent contains a small amount of water, and the ketone derivative is a said enol ester.

35. A process according to claim 34 wherein the solvent is formic acid and the small amount of water is up to 3% water.

36. A process according to claim 25 wherein the process is carried out at a temperature of from −45° C. to +80° C. and the molar ratio of fluorine to enol ester or trialkylsilyl ether is from 0.5:1 to 6:1.

37. A process for the preparation of an α-fluoroketone of formula R—CHFC=O.R' comprising:

converting a ketone of formula R—CH$_2$C=O.R into a ketone derivative which is an enol ester of formula R—CH=C(OCO.R")R' or is a trialkylsilyl ether of formula R—CH=C(OSiR"$_3$).R' wherein R and R' are independently selected from alkyl, substituted alkyl, cycloalkyl, substituted cycloalkyl, aryl and substituted aryl, said substituents being another said R/R' group, halogen, alkoxy or aryloxy, or wherein groups R and R' together form a cyclic structure, and R" is alkyl or cycloalkyl; and reacting that ketone derivative, dissolved in acetonitrile or formic acid, with elemental fluorine.

38. A process according to claim 37 wherein R and R' contain up to 10 carbon atoms, R" has from 1 to 4 carbon atoms, and the elemental fluorine is fluorine gas diluted with an inert gas.

* * * * *